(12) United States Patent
Galvin et al.

(10) Patent No.: US 6,239,144 B1
(45) Date of Patent: May 29, 2001

(54) METHODS OF TREATING BONE LOSS

(75) Inventors: Rachelle J Galvin, Indianapolis; Bruce D Gitter, Carmel, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/319,388

(22) PCT Filed: Apr. 3, 1998

(86) PCT No.: PCT/US98/06674

§ 371 Date: May 27, 1999

§ 102(e) Date: May 27, 1999

(87) PCT Pub. No.: WO98/43639

PCT Pub. Date: Oct. 8, 1998

Related U.S. Application Data

(60) Provisional application No. 60/043,909, filed on Apr. 3, 1997.

(51) Int. Cl.[7] .................. A61K 31/445; A61K 31/495; A61K 31/50; A61K 43/00
(52) U.S. Cl. ................ 514/315; 514/254; 514/419
(58) Field of Search .................... 514/254, 315, 514/419

(56) References Cited

U.S. PATENT DOCUMENTS

| | | | |
|---|---|---|---|
| 5,472,978 | 12/1995 | Baker et al. | 514/443 |
| 5,530,009 | 6/1996 | Cho et al. | 514/316 |
| 5,612,336 | 3/1997 | Lewis et al. | 514/235.2 |
| 5,627,211 | 5/1997 | Teall | 514/539 |
| 5,712,288 | 1/1998 | Emonds-Alt et al. | 514/305 |

FOREIGN PATENT DOCUMENTS

| | | |
|---|---|---|
| WO 95/14017 | 5/1995 | (WO) . |
| WO 96/01819 | 1/1996 | (WO) . |

OTHER PUBLICATIONS

Joborn, et al., *Acta Endocrinologica (Copenh)*, vol. 124, pp. 54–59 (1991).

Ahren, et al., *Endocrinology*, vol. 113, No. 1, pp. 379–384 (1983).

*Primary Examiner*—Theodore J. Criares
(74) *Attorney, Agent, or Firm*—Manisha A. Desai; Elizabeth A. Dawalt

(57) ABSTRACT

The present invention provides methods of treating or preventing conditions associated with a lack of parathyroid hormone comprising administering to a mammal in need thereof an effective amount of a compound having activity as a tachykinin receptor antagonist. In a most preferred embodiment the present invention provides methods of increasing bone growth in a mammal which comprises administering to a mammal in need thereof an effective amount of a compound having activity as a tachykinin receptor antagonist. Another embodiment of this invention provides methods of treating hyperparathyroidism in a mammal comprising administering to a mammal in need thereof an effective amount of a compound having activity as a tachykinin receptor antagonist.

10 Claims, No Drawings

METHODS OF TREATING BONE LOSS

PRIORITY CLAIM

This application claims the benefit of U.S. Provisional Patent No. 60/043,909, filed Apr. 3, 1997.

SUMMARY OF THE INVENTION

Tachykinins are a family of peptides which share a common amidated carboxy terminal sequence. Substance P was the first peptide of this family to be isolated, although its purification and the determination of its primary sequence did not occur until the early 1970's.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3):237–243 (1985) for a review of these discoveries.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokmin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

Tachykinins play a major role in mediating the sensation and transmission of pain or nociception, especially migraine headaches. see. e.g., S. L. Shepheard, et al., *British Journal of Pharmacology*, 108:11–20 (1993); S. M. Moussaoui, et al., *European Journal of Pharmacology*, 238:421–424 (1993); and W. S. Lee, et al., *British Journal of Pharmacology*, 112:920–924 (1994).

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instabilty.

Recent publications have described novel classes of non-peptidyl tachykinin receptor antagonists which generally have greater oral bioavailability and metabolic stability than the earlier classes of tachylinin receptor antagonists. Examples of such newer non-peptidyl tachykinin receptor antagonists are found in U.S. Pat. No. 5,491,140, issued Feb. 13, 1996; U.S. Pat. No. 5,328,927, issued Jul. 12, 1994; U.S. Pat. No. 5,360,820, issued Nov. 1, 1994; U.S. Pat. No. 5,344,830, issued Sep. 6, 1994; U.S. Pat. No. 5,331,089, issued Jul. 19, 1994; European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; Patent Cooperation Treaty publication WO 93/011609, published Jan. 21, 1993; Canadian Patent Application 2154116, published Jan. 23, 1996; European Patent Publication 693,489, published Jan. 24, 1996; and Canadian Patent Application 2151116, published Dec. 11, 1995.

It is known that even in the adult human, bone is subject to turnover. In certain locations, such as the internal auditory capsule, there is apparently no turnover after the organ is formed. In other locations, particularly in the central skeletal axis, the turnover appears to continue during adulthood. Bone turnover occurs on the surface of the existing bone matrix, which is composed of protein (mainly collagen) and minerals. Bone turnover is initiated with the destruction of bone matrix by osteoclasts. The osteclast is a multinucleated cell which secretes acid and proteolytic enzymes leading to the lysis of the collagen matrix protein and the release of minerals into the extracellular fluid compartment. Following this initial phase of bone destruction, or resorptive phase, formation of new bone protein matrix sets in. New bone proteins are deposited, and sometime later, minerals begin to be incorporated into the newly formed matrix. The formation of bone matrix and its subsequent mineralization are functions of osteoblasts, which are mononucleated cells. The formation phase is often followed by a period of inactivity (1,2). In vivo, resorption appears to be tightly coupled with formation (3) and bone turnover is thus a succession of events, the location of which is known as the Bone Metabolism Unit or the BMU. Osteoblasts and osteoclasts, the putative mediators of bone turnover are thought to belong to two distinct cell lineages. These two cell types are not preformed cells, but they differentiate from their precursors through cell activation.

Bone matrix can either be maintained by a cessation of bone turnover as for the bone of the internal auditory capsule, or by a balance between resorption and formation. In many studies on skeletal changes in relation to age, a gain in the total body bone volume is observed during the growth period and the skeletal mass readies a maximum during early adulthood. This gain is followed by a fall in bone volume with age. In females, a phase of more rapid bone loss often occurs during the perimenopausal period before a slower steadier phase. For this reason, bone loss in the female tends to be more severe than in the male. An understanding of bone balance in the BMU may thus be critical to understanding the pathogenesis of skeletal aging. In any case, mechanisms controlling bone turnover are complex and are not well understood at this time. The complexity of the control mechanisms has resulted in a variety of approaches to reducing bone loss.

Bone turnover can be regulated at two different stages. It can be regulated at the stage of the activation of precursor cells. Regulators of cellular activation can control not only the number of active BMU in the skeleton, but possibly also the number of osteoclasts and osteoblasts in an individual BMU. Bone turnover secondly can be regulated at the level of differentiated bone cells. The complexity of the bone cell system makes the separate study of these two levels of regulation difficult.

Regulators of bone cells appear to fall into two categories. The first type interacts with specific receptors on cell membranes. One class of these regulators acts through the adenylate cyclase system with the generation of intracellular cyclic AMP as the second messenger acting on the protein kinase K system. Parathyroid hormone (PTH) and calitonin (CT) belong to this class. A second class also interacts with a membrane receptor and results in the intracellular release of a molecule derived from phosphoinositides which in turn leads to an increase in intracellular calcium and activation of Kinase C. A third class involves interaction of the regulator with a cell surface receptor, but the second signal is generated by the receptor molecule itself with the subsequent activation of tyrosine Kinase. Many of the growth factors appear to act in this way (8–15). Regulators falling into the second category do not interact with a cell membrane receptor, but can cross the cell membrane to bind with a cytosolic receptor. The regulator is then transported across the nuclear membrane by the cytosolic receptor to interact with the DNA resulting in increased transcription of specific genes. Steroid hormones, including vitamin D, appear to act in this manner.

Many hormones stimulate the proliferation of osteoclasts. These include 1,25(OH)2D, PTH and prostaglandins. PTH and 1,25(OH)2D receptors in osteoclasts have apparently not yet been identified. These two hormones seem to have no effect on osteoclasts in culture. However, when osteoclasts are co-cultured with osteoblast-like cell lines, PTH and 1,25(OH)2D stimulate the proliferation of osteoclasts. IL-1 and TNF appear to act in a similar way as PTH and 1,25(OH)2D. Other growth factors, like EGF, TFG and PDGF appear to stimulate osteoclasts through increased production of PGE. Calcitonin and corticosteroids are known osteoclast inhibitors along with chemicals such as diphosphonates.

It is currently believed that interleukin 1 may stimulate collagen and non-collagen bone protein and DNA synthesis. The effect on bone protein synthesis is blocked by indomethacin, suggesting that this action of IL-1 is mediated through PGE. Indomethacin seems to have no effect on the IL-1 effect on osteoblast DNA synthesis. In culture studies on osteoblast-like cell lines suggest that some locally produced growth factors stimulate DNA and collagen synthesis. In bone cell culture, PTH or Vitamin D suppresses collagen synthesis. This in vitro effect of PTH contrasts with the in vivo effect observed in human subjects and experimental animals. It has been demonstrated in rats and in human hyperparathyroid patients that PTH can stimulate the deposition of demineralized bone matrix. Preliminary clinical trial studies on the efficacy of the PTH 1–34 amino acid fragment in the treatment of osteoporosis indicate that this PTH fragment can increase the trabecular volume. The reason for this discrepancy is not yet fully explained.

Parathyroid hormone is a peptide of 84 amino acids in its mature form. Initially translated pre-pro-parathyroid hormone is much larger, the pre sequence being a signal sequence which is cleaved when the peptide enters the rough endoplasmic reticulum. In the golgi apparatus, the pro-sequence is cleaved off leaving the intact mature hormone packaged in the secretory granule. It appears that regulation of the rate of secretion is governed not so much by the rate of production of the intracellular peptide, but in the rate of intracellular destruction and in the rate of secretion. Intracellularly, the mature peptide is truncated at both the amino and the carboxyl termini. The truncated peptide may be secreted into circulation as an inactive fragment. The secretion of the mature peptide can be stimulated by a drop in the extracellular calcium concentration. An elevated serum calcium concentration on the other hand appears to suppress the secretion of PTH. Once in circulation, the mature peptide is rapidly cleaved in the liver at many sites of the molecule including the region of the 38 amino acid residue. The smaller fragment at the amino terminal end, which includes the first 34 amino acids, carries the full known biological activity in terms of its action on the kidney, the intestine and the bone. It also binds fully to the cell membrane receptor to stimulate cAMP production. The level of the 1–38 fragment in the serum is normally immeasurable indicating that it has a short circulatory life. The larger inactive carboxyl terminal fragment has a relatively long half life and carries the highest proportion of the immunoreactive PTH in the circulatory system. All fragments in circulation are eventually destroyed in the kidney and the liver. One of the renal mechanisms for elimination of the circulating inactive PTH fragments is glomerular filtration.

PTH participates in calcium and skeletal homeostasis. PTH stimulates the tubular resorption of calcium by the kidney and inhibits the reabsorption of phosphate and bicarbonate by the proximal renal tubules. A second effect of PTH on the kidney is the stimulation of 1,25(OH)2D production. This vitamin D metabolite is an in vivo stimulator of osteoclasts as well as an enhancer of intestinal calcium absorption. The increase in calcium absorption by the intestine following PTH stimulation is mediated by this vitamin D metabolite. In vivo, PTH stimulates osteoclastic bone resorption with the release of calcium into the circulation. PTH also causes proliferation of osteoblasts. In many cases of hyperparathyroidism there is a skeletal loss. However, an increase in spinal density has been reported in some cases of primary hyperparathyroidism as well as in secondary hyperparathyroidism complicating renal failure. Kalu and Walker have observed that chronic administration of low doses of parathyroid extract led to sclerosis of bone in the rat. Tam et al., [*Metabolism* 27, 14, (1978)] studied the effect of low calcium diet on the bone mineral apposition rate in the rat by tetracycline labeling and found that despite the loss of bone due to increase in bone resorption histologically (as a result of secondary hyperparathyroidism), the bone mineral apposition rate was increased. It was also found that the bone mineral apposition rate was increased in 23 human patients with mild primary hyperparathyroidism. After successful removal of parathyroid adenoma from four of the patients, the rate returned to the level observed in control subjects. There has also been found to be a dose dependent stimulation of the mineral apposition rate by PTH. The potency of the 1–34 fragment and the intact PTH hormone appears to be about the same on a molar basis. This is consistent with the 1–34 fragment of the PTH molecule carrying the biological activity of the intact hormone. It has also been observed that the end result of the administration of PTH on skeletal homeostasis depends on how the hormone is administered. For the same daily dose, the bone volume shows a dose dependent increase if the daily dose of the hormone is given as one single injection. However, when the same daily dose is administered by continuous infusion with a subcutaneous mini-osmotic pump, the result is bone loss. Intermittent injection causes practically no effect on the serum calcium levels whereas infusion causes a dose dependent increase in the serum calcium. The effects of PTH administered by these two routes on bone mineral apposition rate as measured by tetracycline labeling are the same. What accounts for this differential effect is not understood.

Given the general understanding of bone growth and its regulation, various approaches to treatment of diseases involving reduction of bone mass and accompanying disorders are exemplified in the patent literature. For example, PCT Patent Application No. 9215615 published Sep. 17, 1992 describes a protein derived from a porcine pancreas which acts to depress serum calcium levels for treatment of bone disorders that cause elevation of serum calcium levels. European Patent Application No. 504938 published Sep. 23, 1992 describes the use of di- or tripeptides which inhibit cysteine protease in the treatment of bone diseases. PCT Patent Application No. 9214481 published Sep. 3, 1992 discloses a composition for inducing bone growth, the composition containing activin and bone morphogenic protein. European Patent Application No. 499242 published Aug. 19, 1992 describes the use of cell growth factor compositions thought to be useful in bone diseases involving bone mass reduction because they cause osteoblast proliferation. PCT Patent Application No. 4039656 published Jun. 17, 1992 describes a drug containing the human N-terminal PTH fragment 1–37. European Patent Application No. 451867 published Sep. 16, 1991 describes parathyroid hormone peptide antagonists for treating dysbolism associated with calcium or phosphoric acid, such as osteoporosis.

SUMMARY OF THE INVENTION

The present provides methods of treating or preventing conditions associated with a lack of parathyroid hormone comprising administering to a mammal in need thereof an effective amount of a compound having activity as a tachykinin receptor antagonist.

In a most preferred embodiment the present invention provides methods of increasing bone growth in a mammal which comprises administering to a mammal in need thereof an effective amount of a compound having activity as a tachykinin receptor antagonist.

Another embodiment of this invention provides methods of treating hyperparathyroidism in a mammal comprising administering to a mammal in need thereof an effective amount of a compound having activity as a tachykinin receptor antagonist.

DETAILED DESCRIPTION AND PREFERRED EMBODIMENTS

The present invention teaches that tachykinin receptor modulators influence the secretion of parathyroid hormone. The present invention specifically teaches that tachykinin receptor antagonists increase the secretion of PTH and, therefore, tachykinin receptor antagonists are useful as PTH secretagogues.

The methods of the present invention may employ any of various tachykinin receptors. In recent publications many different groups of non-peptidyl tachykinin receptor antagonists have been described.

Patent Cooperation Treaty publication WO 94/01402, published Jan. 20, 1994, describes a series of compounds best typified by the following compound.

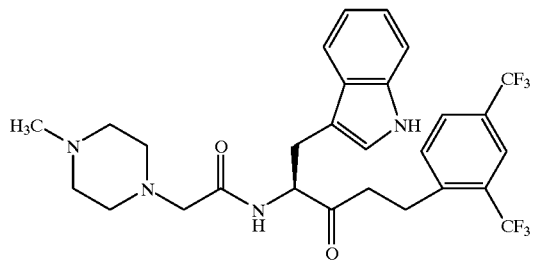

European Patent Publication 591,040 A1, published Apr. 6, 1994 describes a series of compounds typified by the following compound:

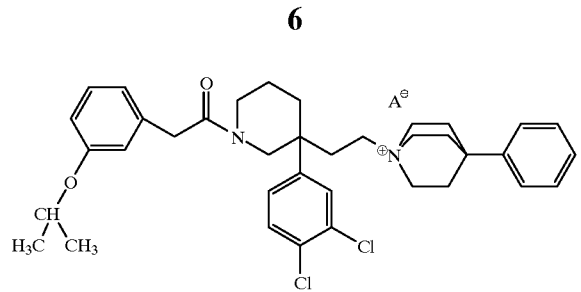

where $A^\ominus$ is a pharmaceutically acceptable anion.

Patent Cooperation Treaty publication WO 94/04494, published Mar. 3, 1994, describes a series of compounds typified by the following compound.

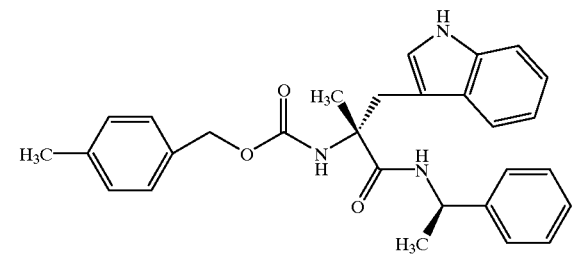

Patent Cooperation Treaty publication WO 93/01169, published Jan. 21, 1993, describes a series of compounds typified by the following compound.

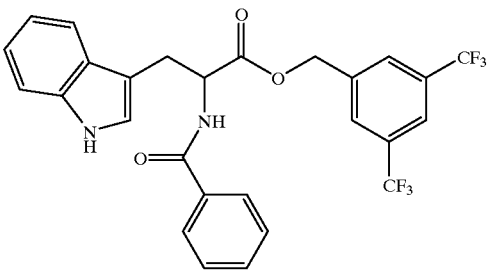

Another group of tachykini receptor antagonists is characterized by the compound of the formula:

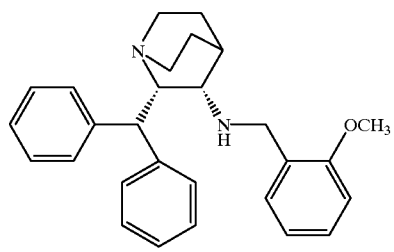

having the designation (±)-CP 96345. These compounds and their syntheses are described in E. J. Warawa, et al., *Journal of Medicinal Chemistry*, 18:357 (1975).

Yet another group of tachykinin receptor antagonists is characterized by the compound of the formula:

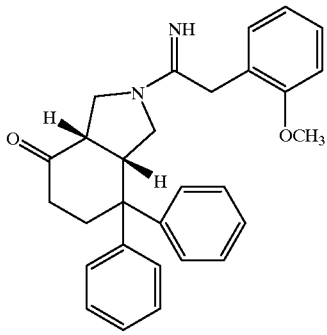

having the designation RP 67580. These compounds and their syntheses are described in C. Garret, et al., *Proceedings of the National Academy of Sciences (USA)*, 88:10208–10211 (1991) and the references cited therein.

Patent Cooperation Treaty publication WO 94/07843 describes a series of cyclohexylamine derivatives typified by the following compound

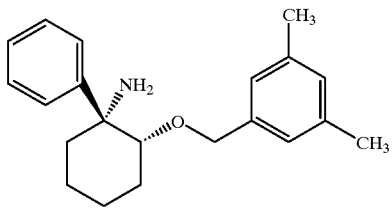

which are useful as tachykinin receptor antagonists.

Another group of compounds useful as tachykinin receptor antagonists is typified by the following compound.

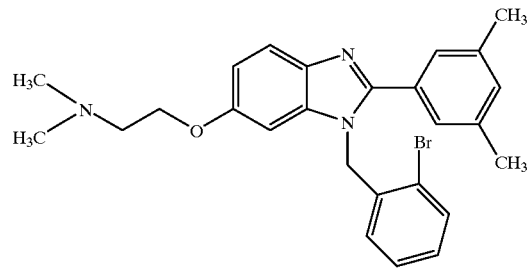

The synthesis of these compounds is described in European Patent Publication EP 694,535, published Jan. 31, 1996.

The following compound has been shown to be effective as an NK-1 antagonist useful as an anti-emetic.

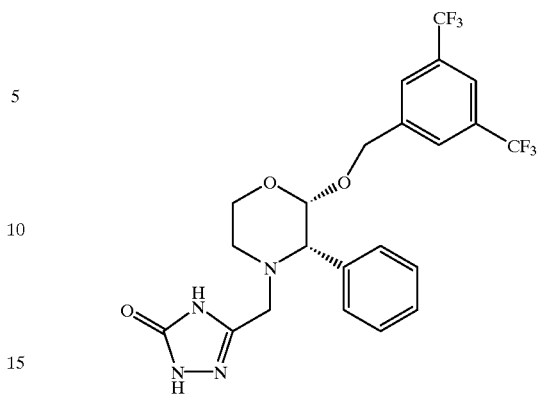

This compound is 2-(S)-[(3,5-bis(trifluoromethylmethyl)benzyl)oxy]-3(S)-phenyl-4-[(3-oxo-1,2,4-triazol-5-yl)methyl]morpholine and is referred to as L-742,694. This compound is described in J. J. Hale, et al., *Journal of Medicinal Chemistry*, 39:1760–1762 (1996).

The compound MDL 103,896 is described as an NK-1 antagonist that is useful in the treatment or prevention of allergies. This compound, having the structure

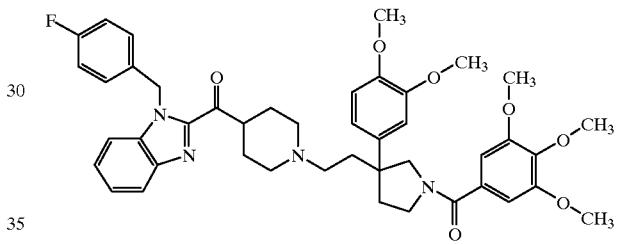

is described as having some histamine H1 receptor antagonist activity as well as the tachykinin receptor antagonist activity.

The compound (S)-1-(2-methoxybenzyl)-2-[(4-phenyl-1-piperaziyl)methyl]-4-(1H-indol-3-ylmethyl)-2-imidazoline and related compounds are described as effective tachykinin receptor antagonists in European Patent Publication 699,665, published Mar. 6, 1996. This compound has the following structure.

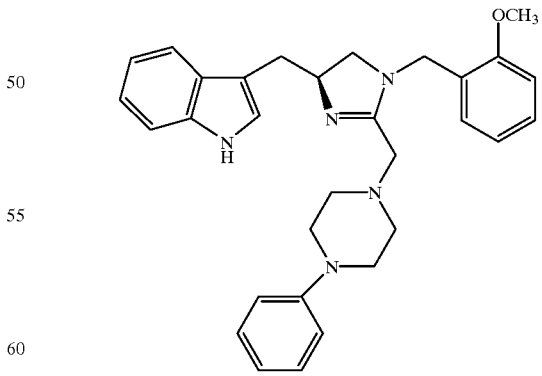

The above groups of compounds are only illustrative of the tachykinin receptor antagonists which are currently under development. This listing of groups of compounds is not meant to be comprehensive, the methods of the present invention may employ any tachykinin receptor antagonist and is not limited to any particular class of compound.

A most preferred class of tachykinin receptor antagonists are those compounds of the following structure

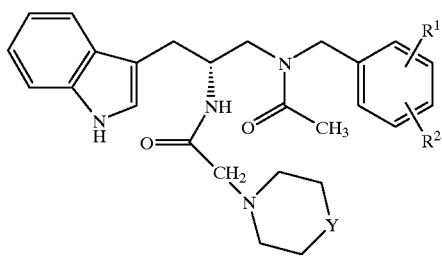

where $R^1$ and $R^2$ are independently selected from the group consisting of hydrogen, methyl, methoxy, chloro, and trifluoromethyl, with the proviso that no more than one of $R^1$ and $R^2$ can be hydrogen; and Y is

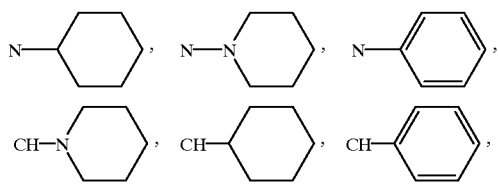

N—$R^a$, or CH—NR$^b$R$^c$, where $R^a$, $R^b$, and $R^c$ are independently selected from the group consisting of hydrogen and $C_1$–$C_6$ alkyl; or a pharmaceutically acceptable salt or solvate thereof. The synthesis of these compounds is described in Patent Cooperation Treaty Publications WO 95/14017, published May 26, 1995, and WO 96/01819, published Jan. 25, 1996.

The biological efficacy of a compound believed to be effective as a tachykinin receptor antagonist may be confirmed by employing an initial screening assay which rapidly and accurately measured the binding of the tested compound to known NK-1 and NK-2 receptor sites. Assays useful for evaluating tachykinin receptor antagonists are well known in the art. See. e.g., J. Jukic, et al., *Life Sciences*, 49:1463–1469 (1991); N. Kucharczyk, et al., *Journal of Medicinal Chemistry*, 36:1654–1661 (1993); N. Rouissi, et al., *Biochemical and Biophysical Research Communications*, 176:894–901 (1991).

NK-1 Receptor Binding Assay

Radioreceptor binding assays were performed using a derivative of a previously published protocol. D. G. Payan, et al., *Journal of Immunology*, 133:3260–3265 (1984). In this assay an aliquot of IM9 cells ($1\times10^6$ cells/be in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well characterized cell line which is readily available to the public. See. e.g., *Annals of the New York Academy of Science*, 190: 221–234 (1972); *Nature (London)*, 251 :443–444 (1974); *Proceedings of the National Academy of Sciences (USA)*, 71:84–88 (1974). These cells were routinely cultured in RPMI 1640 supplemented with 50 µg/ml gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, were grown in 75 cm$^2$ flasks or roller bottles in minimal essential medium (alpha modification) with 10% fetal bovine serum. The gene sequence of the human NK-2 receptor is given in N. P. Gerard, et al., *Journal of Biological Chemistry*, 265:20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets were washed once using the above procedure, and the final pellets were resuspended in 100–120 ml 50 mM Tris buffer, pH 7.4, and 4 ml aliquots stored frozen at −70° C. The protein concentration of this preparation was 2 mg/ml.

For the receptor binding assay, one 4-ml aliquot of the CHO-hNK-2R membrane preparation was suspended in 40 ml of assay buffer containing 50 mM Tris, pH 7.4, 3 mM manganese chloride, 0.02% bovine serum albumin (BSA) and 4 µg/ml chymostatin. A 200 µl volume of the homogenate (40 µg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 µl; the final concentration in the assay was 20 pM. Non-specific binding was determined using 1 µM eledoisin. Ten concentrations of eledoisin from 0.1 to 1000 nM were used for a standard concentration-response curve.

All samples and standards were added to the incubation in 10 µl dimethylsulfoxide (DMSO) for screening (single dose) or in 5 µl DMSO for $IC_{50}$ determinations. The order of additions for incubation was 190 or 195 µl assay buffer, 200 µl homogenate, 10 or 5 µl sample in DMSO, 100 µl radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 ml of cold 50 mM Tris buffer, pH 7.7. The filter circles were then punched into 12×75 mm polystyrene tubes and counted in a gamma counter.

In Vitro PTH Secretion Assay

Porcine parathyroid glands were collected at a slaughterhouse, dipped in 70% ethanol, and then in chilled isolation medium [Ham's F-12 medium (Gibco BRL) containing 1 mM $MgCl_2$ and 20 mM HEPES, pH 7.4], containing 1.25 mM $Ca^{2+}$. The glands were then trimmed of fat and connective tissue and stored on ice in isolation medium containing 1.25 mM $Ca^{2+}$ for approximately 2.5 hours.

Parathyroid cells were isolated from bovine or porcine glands as described by J. Zhang, et al., Endocrinology, 133:152–158 (1993). The glands were minced and the digested for two hours at 37° C. using 3 mg/ml of collagenase type I and 20 mg/ml DNase I in isolation medium containing 1.3 mM CaCl2. The glands were vigorously pipetted every 20 minutes during incubation. The cells were then passed through a 100 µm mesh and centrifuged at 100×g for 10 minutes. The cell pellet was washed once in isolation medium containing 3 mM CaCl2 and 1.0% heat-inactivated fetal bovine serum (FBS, Hyclone) followed by a centrifugation at 50×g. The number of viable cells was then evaluated using Trypan Blue exclusion and cell plating was based on the viable cell count. The cells were seeded in tissue culture dishes at $1.9-2.2 \times 10^5$ cells/cm$^2$.

The porcine cells were seeded in growth medium [Ham's F-12 containing 1 mM MgCl$_2$, 20 mM HEPES, 10% FBS, and 1% antibiotic/antimycotic] which contained 1.75 mM CaCl$_2$. The cells were maintained overnight in a 37° C. humidified incubator with 5% carbon dioxide. The following day the medium was removed and the cells were treated for three hours with medium containing various calcium concentrations (0.5–3 mM) and/or test agents. The culture medium was then collected, passed through MultiScreen Filtration plates (Millipore), and the filtrate was analyzed for PTH using a IRMA assay from Nichols Institute.

PTH Secretion in Culture or Bovine Parathyroid Cells

Primary monolayer cell cultures of bovine parathyroid cells are prepared according to the method of MacGregor, et al. with minor modifications. MacGregor et al, "Primary Monolayer Cell Culture of Bovine Parathyroids: Effects of Calcium Isoproterenol and Growth Factors", *Endocrinology* 30:313–328 (1983). Briefly, bovine parathyroid glands are tried of extraneous tissue, sliced to ~0.5 mm thickness with a Stadie-Riggs tissue slicer (Thomas Scientific, Swedesboro, N.J.) and placed in DME (HG)/Ham's F-12 culture medium (50/50) containing 2.5 mg/ml collagenase (Boehringer Mannheim, Indianapolis, Ind.) and 0.5 mM total calcium. The suspension (1 g tissue per 10 ml media) is agitated in a shaking water bath at 37° for 90 minutes, and periodically aspirated through a large bore hole cut in an Eppendorf pipet tip attached to a 60-ml syringe. The digested tissue is filtered through gauze, resuspended, and washed three times with culture medium containing DME (HG)/Ham's F12 medium (50/50), 1 mM total calcium, 4% newborn calf serum, 15 mM HEPES, 100 IU/ml penicillin, 100 µg/ml streptomycin, 5 µg/ml insulin, 2 mM glutamine, and 1% nonessential amino acids. Cells are plated at 80,000 cells/cm$^2$. After 24 hours, the medium is replaced with the same medium as described above, with the exception that the serum is replaced with 1 mg/ml bovine serum albumin and 5 µg/ml holotransferrin. This medium is replenished every 24 to 48 hours.

PTH Secretion Studies

The test media, containing various concentrations of test compound are prepared by adding the indicated ethanol solutions of the compounds to the media; final ethanol concentration is 0.1%. After incubation, media are collected, centrifuged, and then stored at –20° C. until analyzed for PTH. PTH is assayed using antibody CH9, which recognizes intact, mid-region, and carboxy-terminal fragments of PTH. Details of the recognition characteristics of the antisera and the radioimmunoassay (RIA) methodology have been described previously in Hruska et al, "Metabolism of Immunoreactive Parathyroid Hormone in the Dog. The Role of the Kidney and the Effects of Chronic Renal Disease", *Journal of Clinical Investigations*, 56:39–48 (1975). Cellular protein in each sample is determined by sonicating the cells into 1 mM sodium hydroxide and assaying an aliquot by using a protein assay kit (Bio-Rad Laboratories, Richmond, Calif.). All PTH values are corrected for cell protein.

Determination of Anabolic Activities of Test Compounds with Ovariectomized (OVX) Rat Model A full description of the protocol is given in Rixon, et al (1994), *J. Bone*, 9, 1179–1189, incorporated herein by reference. Sprague-Dawley rats weighing 255–275 g are purchased from Charles River (St. Constant, QC, Canada). For each experiment, 105 rats are weighed and divided into 21 groups, each with 5 rats, with comparable mean body weights between 260 and 265 g. These 21 groups are divided into 6 experimental groups consisting of 1 group of 5 animals for O-time controls and 5 groups of 20 rats each which provided one group for normal or sham-ovariectomized (Sham-OVX) controls, one for OVX controls, and 3 for OVX rats treated with various test compounds.

Sham OVX and OVX are performed under anesthesia by the standard dorsal approach. For sham-OVX, the ovaries are exteriorized, but not removed. Except for the normal, unoperated rats, day 0 for each experimental group is the day of OVX. Starting 2 weeks later, designated groups of rats are given daily subcutaneously injections of test compounds (1 nmole/100g of body weight) dissolved in acidic saline (0.15M NaCl containing 0.001N HCl). The OVX control animals received comparable volumes of diluent solution only.

The preparation and analysis of cortical and trabecular bone is carried out as described in M. Gunness-Hey & J. M. Hock, *Metab. Bone Dis. Rel. Res.*, 5, 177–181 (1984), incorporated herein by reference. Femurs are isolated, cleaned, and their lengths from the proximal, collum femoris to the distal condylar surfaces are measured. Each bone is then cut in half at mid-diaphysis and the proximal half discarded. After removing the epiphysis, each half-femur is split lengthwise and the marrow washed out with distilled water. Each half is placed under a dissecting microscope and the trabecular (cancellous) bone is scraped out. The isolated trabecular bone and the remaining cortical (compact bone) are dried at 55° C. for at least 24 hr., and weighed to determined dry mass, expressed as mg/distal half-femur.

After at least 3 days, the trichloroacetic acid extract is quantitatively removed and saved. The calcium contents of the pooled tricloroacetic acid extracts from each cortical and trabecular bone sample are measured using the cresolphthalein complex one colorimetric procedure, using a kit from CIBA-Corning Diagnostics.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
|---|---|
| Active Ingredient(s) | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
|---|---|
| Active Ingredient(s) | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
|---|---|
| Active Ingredient(s) | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
|---|---|
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient(s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositores, each containing 25 mg of active ingredient are made as follows:

| Ingredient | Amount |
|---|---|
| Active Ingredient(s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
|---|---|
| Active Ingredient(s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystaline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
|---|---|
| Active Ingredient(s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
|---|---|
| Active Ingredient(s) | 250.0 mg |
| Isotonic saline | 1000 ml |

Formulation Preparation 10

A topical formulation may be prepared as follows:

| Ingredient | Quantity |
|---|---|
| Active Ingredient(s) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
|---|---|
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous string and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, caxbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compounds, and the state of the patient.

We claim:

1. A method for the treatment of a condition associated with a deficiency of parathyroid hormone in a mammal which comprises administering to a mammal in need thereof an effective amount of a compound or composition having activity as a tachykinin receptor antagonist.

2. A method as claimed in claim 1 wherein the compound having activity as a tachykinin receptor antagonist is (R)-2-[N-(2-((4-cycdohexyl)piperazin-1-yl)acetyl)amino]-3-(1H-indol-3-yl)-1-[N-(2-methoxybenzyl)acetylamino]propane, (R)-3-(1H-indol-3-yl)-1-[N-(2-methoxybenzyl)acetylamino]-2-[N-(2-(4-(piperidin-1-yl)piperidin-1-yl)acetyl)amino]propane, (R)-3-(1H-indol-3-yl)-1-[N-(2-methoxybenzyl)acetylamio]-2-[N-(2-(4-(piperidin-1-yl)piperidin-1-yl)acetyl)amino]propane dihydrohloride trihydrate, 1-(2-bromobenzyl)-2-(3,5-dimethylphenyl)-6-[2-(N,N-dinethylamino)ethoxy]benzidazole, RP 67580, (±)CP 96345, 5-(3,5-bistrifuoromethylphenyl)-1-(3-indolyl)-2-((4-methylpiperazin-1-yl)acetamido)-3-pentanone, (4-methylphenyl)methyl [R-(R*,S*)]-[1-(1H-indol-3-ylmethyl)-1-methyl-2-oxo-2-[(1-phenylethyl)amino]ethyl]carbamate, (S)-1-(2-methoxybenzyl)-2-[(4-phenyl-1-piperazinyl)methyl]-4-(1H-indol-3-ylmethyl)-2-imidazoline, or 1-(3,5-dimethylbenzyloxy)-2-anmino-2-phenylcydohexane, or a pharmaceutically acceptable salt or solvate thereof.

3. A method as claimed in claim 2 employing (R)-3-(1H-indol-3-yl)-1-[N-(2-methoxybenzyl)acetylamino]-2-[N-(2-(4-(piperidin-1-yl)piperidin-1-yl)acetyl)amino]propane dihydrodhloride trihydrate.

4. A method for enhancing bone growth in a mammal which comprises administering to a mammal in need thereof an effective amount of a compound or composition having activity as a tachykinin receptor antagonist.

5. A method as cained in claim 4 wherein the compound having activity as a tachykinin receptor antagonist is (R)-2-[N-(2-((4-cydohexyl)piperazin-1-yl)acetyl)amino]-3-(1H-indol-3-yl)-1-[N-(2-methoxybenzyl)acetylamino]propane, (R)-3-(1H-indol-3-yl)-1-[N-(2-methoxybenzyl)acetylamino]-2-[N-(2-(4-(piperidin-1-yl)piperidin-1-yl)acetyl)amino]propane, (R)-3-(1H-indol-3-yl)-1-[N-(2-methoxybenzyl)acetylamino]-2-[N-(2-(4-piperidin-1-yl)piperidin-1-yl)acetyl)amino]propane dihydrocloride trihydrate, 1-(2-bromobenzyl)-2-(3,5-dimethylphenyl)-6-[2-(N,N-dimethylamino)ethoxy]benzimidazole, RP 67580, (±)CP 96345, 5-(3,5-bistifiuoromethylphenyl)-1-(3-indolyl)-2-((4-methylpiperazin-1-yl)acetamido)-3-pentanone, (4-methylphenyl)methyl [R-(R*,S*)]-[1-(1H-indol-3-ylmethyl)-1-methyl-2-oxo-2-[(1-phenylethyl)amino]ethyl]carbamate, (S)-1-(2-methoxybenzyl)-2-[(4-phenyl-1-piperazinyl)methyl]-4-(1H-indol-3-ylmethyl)-2-imidazoline, or 1-(3,5-dimethylbenzyloxy)-2-amino-2-phenylcyclohexane, or a pharmaceutically acceptable salt or solvate thereof.

6. A method as daimed in claim 5 employing (R)-3-(1H-indol-3-yl)-1-[N-(2-methoxybenzyl)acetylamio]-2-[N-(2-(4(piperidin-1-yl)piperidin-1-yl)acetyl)amino]propane dihydrochloride trihydrate.

7. A method for treating hyperparathyroidism in a mammal which comprises administering to a mammal in need thereof an effective amount of a compound or composition having activity as a tachykinin receptor antagonist.

8. A method as daimed in claim 7 wherein the compound having activity as a tachykinin receptor antagonist is (R)-2-[N-(2-((4-cydohexyl)piperazin-1-yl)acetyl)amino]-3-(1H-indol-3-yl)-1-[N-(2-methoxybenzyl)acetylamino]propane, (R)-3-(1H-indol-3-yl)-1-[N-(2-methoxybenzyl)acetylamino]-2-[N-(2-(4-piperidin-1-yl)piperidin-1-yl)acetyl)amino]propane, (R)-3-(1H-indol-3-yl)-1-[N-(2-methoxybenzyl)acetylamino]-2-[N-(2-(4-piperidin-1-yl)piperidin-1-yl)acetyl)amino]propane dihydrochloride trihydrate, 1-(2-bromobenzyl)-2-(3,5-dimethylphenyl)-6-[2-(N,N-dimethylamino)ethoxy]benzimidazole, RP 67580, (±)CP 96345, 5-(3,5-bistrifluoromethylphenyl)-1-(3-indolyl)-2-((4-methylpiperazin-1-yl)acetamido)-3-pentanone, (4-methylphenyl)methyl [R-(R*,S*)]-[1-(1H-indol-3-ylmethyl)-1-methyl-2-oxo-2-[(1-phenylethyl)amino]ethyl]carbamate, (S)-1-(2-methoxybenzyl)-2-[(4-phenyl-1-piperazinyl)methyl]-4-(1H-indol-3-ylmethyl)-2-imidazoline, or 1-(3,5-dimethylbenzyloxy)-2-amino-2-phenylcyclohexane, or a pharmaceutically acceptable salt or solvate thereof.

9. A method as daimed in claim 8 employing (R)-3-(1H-indol-3-yl)-1-[N-(2-methoxybenzyl)acetylamino]-2-[N-(2-(4-(piperidin-1-yl)piperidin-1-yl)acetyl)amino]propane dihydrochloride trihydrate.

10. A method for inducing the secretion of parathyroid hormone in a mammal which comprises administering to a mammal in need thereof an effective amount of a compound or composition having activity as a tachykinin receptor antagonist.

* * * * *